(12) United States Patent
Leahy et al.

(10) Patent No.: US 9,095,330 B2
(45) Date of Patent: Aug. 4, 2015

(54) PERFORATED TUBE FOR CELL COLLECTION

(71) Applicant: Cook Medical Technologies LLC, Bloomington, IN (US)

(72) Inventors: Ronan Leahy, Croom (IE); Donagh O'Sullivan, Ballina-Killaloe (IE)

(73) Assignee: Cook Medical Technologies LLC, Bloomington, IN (US)

( * ) Notice: Subject to any disclaimer, the term of this patent is extended or adjusted under 35 U.S.C. 154(b) by 132 days.

(21) Appl. No.: 13/800,344

(22) Filed: Mar. 13, 2013

(65) Prior Publication Data

US 2014/0276211 A1 Sep. 18, 2014

(51) Int. Cl.
*A61B 10/00* (2006.01)
*A61B 10/04* (2006.01)

(52) U.S. Cl.
CPC ..................... *A61B 10/04* (2013.01)

(58) Field of Classification Search
CPC ..................................................... A61B 10/04
USPC .......... 600/566, 567, 569; 604/529, 264, 267, 604/9, 8, 524, 523; 138/140; 15/104.2, 15/104.16; 401/282, 284
See application file for complete search history.

(56) References Cited

U.S. PATENT DOCUMENTS

| | | | |
|---|---|---|---|
| 3,996,938 A | 12/1976 | Clark, III | |
| 4,465,072 A | 8/1984 | Taheri | |
| D300,060 S | 2/1989 | Molgaard-Nielsen | |
| 4,927,412 A | 5/1990 | Menasche | |
| 4,958,621 A | 9/1990 | Topel et al. | |
| 4,989,614 A | 2/1991 | Dejter, Jr. et al. | |
| 5,037,379 A | 8/1991 | Clayman et al. | |
| 5,048,538 A | 9/1991 | Terwilliger et al. | |
| 5,060,658 A | 10/1991 | Dejter, Jr. et al. | |
| 5,083,572 A | 1/1992 | Pokorny | |
| 5,146,921 A | 9/1992 | Terwilliger et al. | |
| 5,249,583 A | 10/1993 | Mallaby | |
| 5,253,652 A | 10/1993 | Fast | |
| 5,287,857 A | 2/1994 | Mann | |
| 5,423,745 A | 6/1995 | Todd et al. | |
| D360,260 S | 7/1995 | Brandt | |
| 5,488,958 A | 2/1996 | Topel et al. | |
| D369,857 S | 5/1996 | Booth et al. | |
| 5,535,756 A | 7/1996 | Parasher | |
| 5,584,821 A * | 12/1996 | Hobbs et al. | 604/524 |
| 5,628,733 A * | 5/1997 | Zinreich et al. | 604/267 |
| 5,702,413 A | 12/1997 | Lafontaine | |
| 5,713,369 A | 2/1998 | Tao et al. | |
| 5,749,883 A | 5/1998 | Halpern | |
| 5,797,953 A | 8/1998 | Tekulve | |
| 6,346,086 B1 | 2/2002 | Maksem et al. | |
| 6,468,228 B1 | 10/2002 | Topel et al. | |
| 6,685,718 B1 | 2/2004 | Wyzgala et al. | |
| 6,800,083 B2 | 10/2004 | Hiblar et al. | |
| 6,920,662 B2 * | 7/2005 | Moore | 15/104.2 |

(Continued)

*Primary Examiner* — Brian Szmal
(74) *Attorney, Agent, or Firm* — Brinks Gilson & Lione

(57) ABSTRACT

A medical device for collecting cells includes a perforated tube and a brush disposed therein for collecting cells from tissue adjacent the tube. The tube includes a perforated portion and tissue can be drawn into the perforations in response to a vacuum applied to the tube. The brush can be inserted into the tube with the head portion of the brush aligned with the perforated portion to collect cells form the tissue that has been drawn into the perforations by the vacuum. The brush can be removed from the tube and another brush can be inserted to increase cell collection amounts.

28 Claims, 4 Drawing Sheets

(56) References Cited

U.S. PATENT DOCUMENTS

| | | |
|---|---|---|
| 7,252,674 B2 | 8/2007 | Wyzgala et al. |
| 7,641,620 B2 | 1/2010 | Wingler |
| 7,878,983 B2 | 2/2011 | Karpiel |
| 8,034,022 B2 | 10/2011 | Boatman |
| 8,057,496 B2 | 11/2011 | Fischer, Jr. |
| 8,070,691 B2 | 12/2011 | Desilets et al. |
| 8,100,881 B2 | 1/2012 | Hoffa |
| 8,123,769 B2 | 2/2012 | Osborne |
| 8,246,641 B2 | 8/2012 | Osborne et al. |
| 2010/0228179 A1* | 9/2010 | Thomas et al. .......... 604/9 |
| 2014/0336528 A1* | 11/2014 | Sethi .................. 600/566 |

* cited by examiner

PERFORATED TUBE FOR CELL COLLECTION

BACKGROUND

The present invention relates to cell collection devices. More particularly, the invention relates to a perforated tube for collecting cells.

Cell collecting devices, or cytology devices, are well known in the art. A traditional cell collection device can be in the form of a cytology brush. A cytology brush can generally be used by being inserted into a body cavity of a patient, where the brush can contact the body cavity wall to collect cells. Cytology brushes are generally elongate, and include a distal end having a plurality of plastic bristles extending radially outward. The brush can be in the form of a metallic coiled wire, and the bristles can be disposed between the coils. The coiled nature of the brush allows it to generally bend and navigate various tortuous body vessels. Additionally, the coils allow the brush to retain its pushability for delivering the brush through the anatomy.

However, the brushes can be ineffective in collecting a sufficient number of cells and can lead to irritation or bleeding during the cell collection process. The distal end of the brush is generally narrow and has a limited surface area for collecting cells. Moreover, the body vessels for which cell collection is desired can vary greatly from patient to patient. To collect the cells, the brush is inserted into the cavity and brushed against the cavity wall repeatedly, with pressure applied to the wall by the brush so that bristles contact the cavity. This brushing can often lead to bleeding, while collecting only a limited number of desired cells from a limited and inconsistent area of the cavity.

SUMMARY

A system for collecting cells is provided, the system comprising: an elongate tube having a proximal portion and a distal portion and a lumen extending therebetween; an elongate cell collection device including a head portion, the cell collection device disposed within the lumen of the tube; a perforated portion of the tube including a plurality of perforations extending through a sidewall of the tube; and a vacuum source coupled to the tube portion for applying a vacuum to the lumen.

In another form, the perforated portion is disposed substantially around a complete circumference of the tube.

In another form, wherein the perforated portion is disposed around a portion of the circumference of the tube that is less than the complete circumference of the tube.

In another form, the perforated portion is disposed at the distal portion of the tube. In another form, the distal portion of the elongate tube is generally flexible.

In another form, the tube is formed by a sidewall having a thickness of about 0.2 mm to 0.8 mm.

In another form, individual ones of the plurality of perforations have a diameter of about 1-3 mm.

In another form, the distal portion includes a closed end.

In another form, the distal portion of the tube includes a removable tip.

In another form, the cell collection device includes a sealing portion disposed at a distal end thereof that sealingly engages a sidewall of the tube, the tube includes an open distal end, and the sealing portion is moveable distally out of the open distal end of the tube to expose the head portion.

In another form, the head portion comprises a plurality of bristles.

In another form, the lumen has a diameter, and the head portion has a diameter that is greater than the diameter of the lumen.

In another form, the lumen has a diameter, and the head portion has a diameter that is less than or equal to the diameter of the lumen.

In another form, the perforated portion is approximately 1-2 cm long.

In another form, a medical device for collecting cells is provided, the device comprising: an elongate tube having a generally cylindrical sidewall, a proximal portion, and a distal portion, wherein the sidewall defines a lumen extending along the length of the tube; a plurality of perforations disposed in the distal portion and extending through the sidewall; a closed distal tip of the tube disposed distally of the plurality of perforations; an elongate brush disposed within the lumen of the tube, the brush having a shaft with a head portion coupled to a distal end of the shaft for collecting cells disposed within the plurality of perforations; and wherein the perforations extend through the sidewall and the lumen is in fluid communication with an exterior of the tube; and wherein negative pressure applied within the lumen causes body tissue disposed adjacent the exterior of the tube to be presented to the interior of the tube through the perforations.

In another form, individual ones of the plurality of perforations have a generally circular shape and a diameter of approximately 1-3 mm.

In another form, individual ones of the plurality of perforations have a generally slotted shape having a length of approximately 3-10 mm and a width of approximately 1-3 mm.

In another form, the tube is generally flexible and made from pebax.

In another form, the brush is rotatable within the lumen.

In another form, the head portion comprises a plurality of bristles, and an outer circumference of the head portion contacts an inner circumference of the tube.

In another form, a method for collecting cells is provided, the method comprising: inserting an elongate tube into a body cavity, wherein the tube includes a sidewall defining a lumen extending therealong, and wherein the tube includes a perforated portion including a plurality of perforations extending through the sidewall of the tube; longitudinally aligning a head portion of a brush at least partially with the perforated portion of the tube, wherein the head portion overlaps the perforated portion; applying a vacuum to the lumen of the tube; in response to applying the vacuum, drawing body tissue into the plurality of perforations; and in response to drawing the body tissue, contacting the tissue with the brush to collect cells from the tissue.

In another form, the step of aligning the head portion occurs prior to applying the vacuum.

In another form, the step of aligning the head portion occurs after applying the vacuum.

In another form, the method further comprises rotating the head portion.

In another form, the method further comprises retracting the brush from the lumen and inserting a second brush into the lumen and collecting additional cells.

In another form, the method further comprises reciprocating the head portion longitudinally relative to the perforated portion.

In another form, the head portion comprises a plurality of bristles, and the bristles are compressed radially inward with the head portion disposed within the tube.

In another form, the bristles expand outward with the head portion retracted out of the tube.

DETAILED DESCRIPTION

Figure 1:
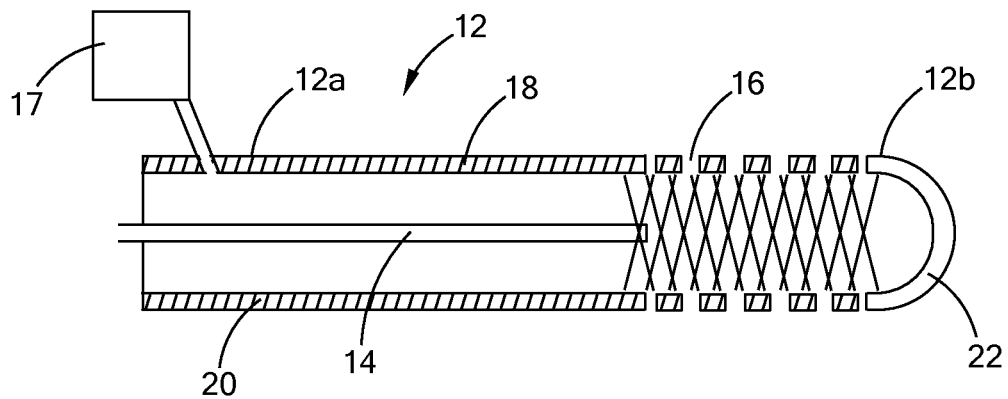
FIG. 1 is a schematic view of a cell collection system including a perforated tube and a brush.

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Referring now to the drawings, FIGS. 1-9 illustrate a cell collection system 10 including an elongate perforated tube 12 and a cytology brush 14 for being inserted into the tube 12 to collect cells. The tube 12 includes a plurality of holes, apertures, or perforations 16 that are disposed through the wall defining the tube 12. The tube 12 is coupled to a vacuum source 17 that can draw adjacent body tissue toward the tube 12 and at least partially into the perforations 16, where the brush 14 can contact the tissue to collect cells therefrom.

Turning now to FIG. 1, the tube 12 includes an elongate generally cylindrical sidewall 18 that defines a lumen 20 extending therealong. The perforations 16 extend through the sidewall 18 of the tube 12 to communicate the exterior of the tube 12 with the lumen 20. The tube 12 includes a proximal portion 12a and a distal portion 12b. The tube 12 can be made from a generally flexible material such as PEBAX or a similar flexible material known in the art and suitable for use within a patient's body. Other possible materials can include PTFE, FEP, PE, nylon, or the like. Alternatively, the tube 12 can be made from a more rigid material depending on the anticipated use of the device 10.

Figure 2:
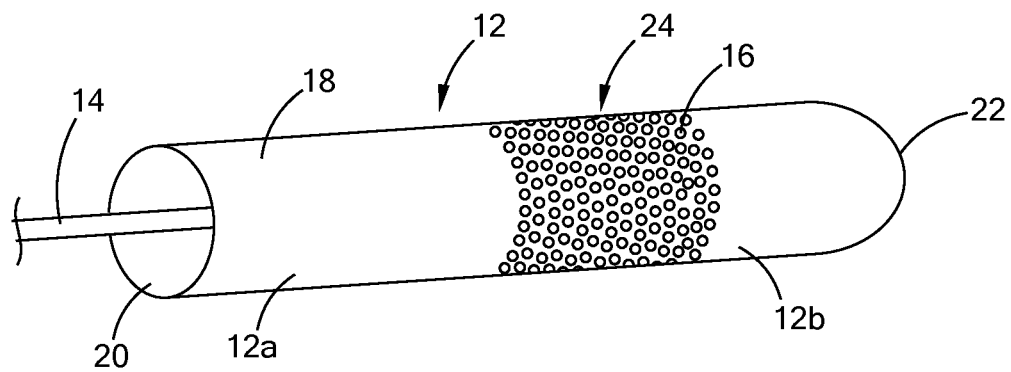
FIG. 2 is an isometric view of the perforated tube.

Turning now to FIG. 2, the distal portion 12b of the tube 12 includes a closed distal end 22 for improving the vacuum effect on the tube 12, which will be described in further detail later. The distal portion 12b is the portion configured for using the vacuum to draw the adjacent body tissue into the perforations 16 for being contacted by the brush 14. The perforations 16 can be disposed about the perimeter of the distal portion 12b so that the perforations 16 generally cover the entire circumference of the distal portion 12b. The perforations 16 thereby define a perforated portion 24 of the tube 12. The perforated portion 24 is disposed proximally from the closed distal end 22 and distally from the proximal portion 12a. Of course, the perforated portion 24 can be disposed at other longitudinal locations along the tube 12.

In one form, the perforations 16 can be disposed about a portion of the circumference of the tube 12. For example, the perforations 16 could cover half of the circumference, allowing for tissue to be drawn in on one side of the tube. It will be appreciated that other amounts of the circumference of the tube 12 can be covered by the perforations 16 to suit the needs of the user.

The tube 12 can have varying lengths depending on the location in the body where cell collection is desired. The perforated portion 24 can be approximately 1-2 cm in length to enable cell collection from an area of similar size. Of course, it will be appreciated that other lengths of the perforated portion 24 could also be used to collect cells from a larger or smaller target length.

The sizing of the tube 12 can depend on the intended location and use of the tube 12. For example, for esophageal or colonic "non-through-the-scope" applications, the length of the tube 12 can be approximately 80 cm with a lumen diameter of about 8-12 mm and a wall thickness of about 0.3-0.8 mm. For duodenal "non-through-the-scope" applications, the length can be about 120 cm with a lumen diameter of about 5-10 mm and a wall thickness of about 0.3-0.8 mm. For biliary or colonic "through-the-scope" applications, the length can be about 230-260 cm with a lumen diameter of about 2-3 mm and a wall thickness of about 0.2-0.5 mm. Of course, it will be appreciated that other sizing can be used to suit the needs of the user.

The perforations 16 can have a diameter of approximately 1 mm in one form. In another form, the perforations 16 can have a diameter between 2-3 mm. Of course, it will be appreciated that other diameters for the perforations 16 could also be used depending on the amount of tissue that is desired to be drawn into the perforations, or the type of tissue. For example, a softer tissue may be more easily drawn into the perforations 16 than a tougher or thicker tissue, so the perforations 16 can be relatively smaller if the target tissue is softer. Conversely, the perforations 16 can be larger to draw harder tissue into the perforations 16.

The size of the perforations 16 relative to the size or material of the tube 12 can vary to provide sufficient structural support for the tube 12. It will be appreciated that there is a tradeoff between the structural integrity of the tube 12 and the number or size of the perforations 16. As the number or size of the perforations 16 increases, the tube 12 can generally become structurally weaker. Conversely, as the number or size of the perforations 16 decreases, the tube 12 can thereby be stronger. These factors are weighed in combination with material selection for the tube 12 and intended use. For example, in one form, the portion of the tube having perforations 16 can be about 5-20 mm long. The shape of the perforations 16 can be circular having a diameter of about 1-3 mm, or the perforations 16 can be slot shaped with a length of about 3-10 mm and a width of about 1-3 mm. The circular and slot shapes can be used in combination, as well as with other shapes having similar sizing. For purposes of discussion, the circular shape will be referenced. The spacing of the perforations 16 can be such that the perforations about 1-5 mm apart; however, other spacing can be used depending on the size of the tube 12 such that the tube 12 does not fracture due to the perforations 16 being too close together.

The amount of cell collection generally depends on the number and size of the perforations 16. As the number and size of the perforations 16 increases, the amount of tissue that is drawn into the perforations 16 increases. However, as stated above, the structural strength of the tube 12 also depends on the number and size of the perforations 16. Thus, there is also a tradeoff between the amount of tissue that is drawn in and the strength of the tube 12. It will thereby be appreciated that there are myriad possibilities for the number and sizes of the perforations 16 available to one skilled in the art without undue experimentation.

Figure 3:
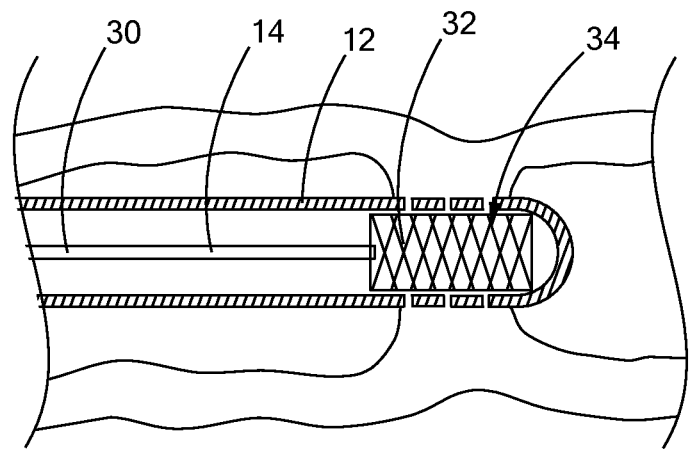
FIG. 3 is a schematic view of the perforated tube and the brush in a cell collecting configuration.

Turning now to FIG. 3, as described above, the system 10 includes the cytology brush 14 which is configured to contact the tissue for cell collection. The brush 14 can be a traditional cytology brush having a shaft 30 and bristles 32. The shaft 30 can be made from a metal or polymer material known in the art capable of being pushed through and retracted from a tubular body, such as the tube 12. The bristles 32 can be made from a plastic material known in the art capable of collecting cells from tissue. The bristles 32 are preferably made from nylon or polyethylene; however, other suitable cytology brush materials could also be used. The bristles 32 can be mounted to the shaft 30 in a manner known in the art, where the bristles 32 will generally extend radially outward from the shaft. In one form, the bristles 32 can be held in place by a friction fit between twists or coils in the shaft 30 (not shown). Of course, it will be appreciated that various other cell collection devices can also be used within the tube 12 to collect cells from tissue that has been drawn into the perforations 16. For example, the cell collection device within the tube could be in the form of a coiled wire, a braided wire, an abraded balloon, a balloon having a perforated sleeve, an absorbable material such as cotton, open or closed cell foam, or the like. However, for the purposes of discussion, the brush 14 will be described.

The brush 14 can have a general overall length corresponding to the length of the tube 12 so that the brush 14 can be inserted within the lumen 20 of the tube 12 along the length of the tube 12 to collect cells from the perforated portion 24. However, other lengths of the brush 14 can be used, as long as the brush 14 is at least long enough for the bristles 32 to reach the perforated portion 24. Of course, in the event the brush 14 is too short, the brush 14 could be inserted through the tube 12 using an auxiliary component that can both push and retract the brush 14. The brush 14 could also include a handle (not shown) to aid in the insertion and retraction of the brush 14 into and out of the tube 12.

The bristles 32 generally define a head portion 34 of the brush 14. The head portion 34 is preferably sized to correspond to the size of the perforated portion 24 so that when the brush 14 is inserted into the tube 12, the head portion 34 will align with the perforated portion 24 to collect cells. However, the head portion 34 could also be shorter or longer than the perforated portion 24 and still successfully collect cells from the tissue drawn into perforations 16 of the tube 12, as long as there is some overlap between the head portion 34 and the perforated portion 24 when the head portion 24 is inserted into the tube 12.

The head portion 34 is preferably wide enough, or has a diameter large enough, to span the diameter or width of the tube lumen 20. In one form, the head portion 34 can be larger than lumen 20. In this form, when the head portion 34 is inserted into the tube 12, the bristles 32 will bend or flex to allow the head portion 34 to fit into the tube 12. With the bristles 32 bent to allow insertion of the head portion 34, the bristles 32 will become biased against the tube 12, thereby allowing for the bristles 32 to contact the body tissue that is drawn into the tube 12 through the perforations 16.

Figure 4:
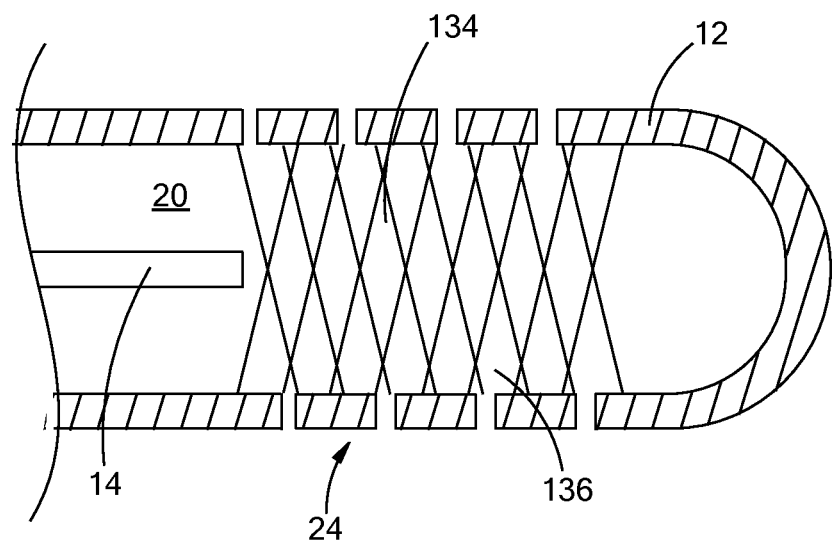
FIG. 4 is a schematic view showing a head portion of the brush disposed within the tube.

In another form, as shown in FIG. 4, a head portion 134 of a brush 114 can be smaller than the lumen 20, thereby defining an annular space 136 between the head portion 134 and the tube 12 when the head portion 134 is centered within the lumen 20. However, during insertion, the head portion 134 can still contact the tube 12 because the head portion 134 is free to shift radially within the tube 12. The user can manually manipulate of reciprocate the brush 114 within the tube 12 to provide additional contact with the perforated portion 24 and the tissue drawn into the perforations 16.

Figure 5:
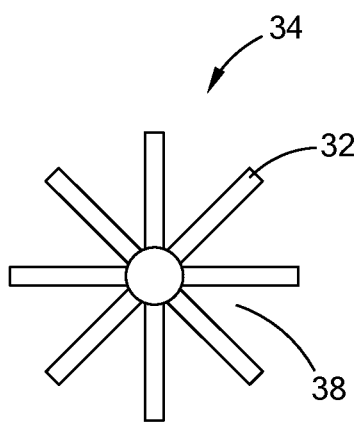
FIG. 5 is a front view of bristles of the brush.
Figure 6:
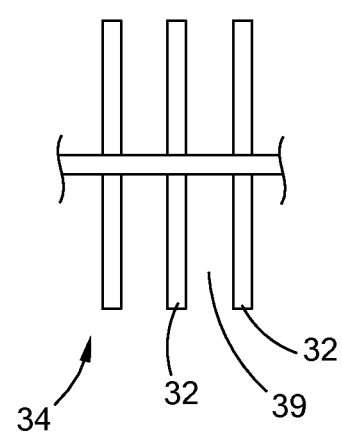
FIG. 6 is a side view of the bristles of the brush.

With reference to FIGS. 5 and 6, the bristles 32 can be arranged such that there is a circumferential space 38 between at least a portion of adjacent bristles 32, as well as a longitudinal space 39 between the bristles 32. These spaces 38, 39 defined between the bristles 32 can allow for airflow longitudinally past the bristles 32 and effectively through the head portion 34. This airflow can allow the vacuum to be applied through the head portion 34 to draw the tissue into the perforations 16 when the brush 14 is inserted. Additionally, the size of the head portion 34 can alter the amount of airflow through the head portion 34. For example, when the head portion 34 width is smaller than the tube 12, the annular space 36 defined between the head portion 34 and the tube 12 can allow for additional airflow. When the head portion 34 is wider than the tube 12 such that the bristles 32 will bend when inserted into the tube 12, the airflow capabilities can decrease. It will therefore be appreciated that the size of the head portion 34 relative to the tube 12 can vary depending on the desired amount of vacuum created along the tube 12.

Figure 7A:
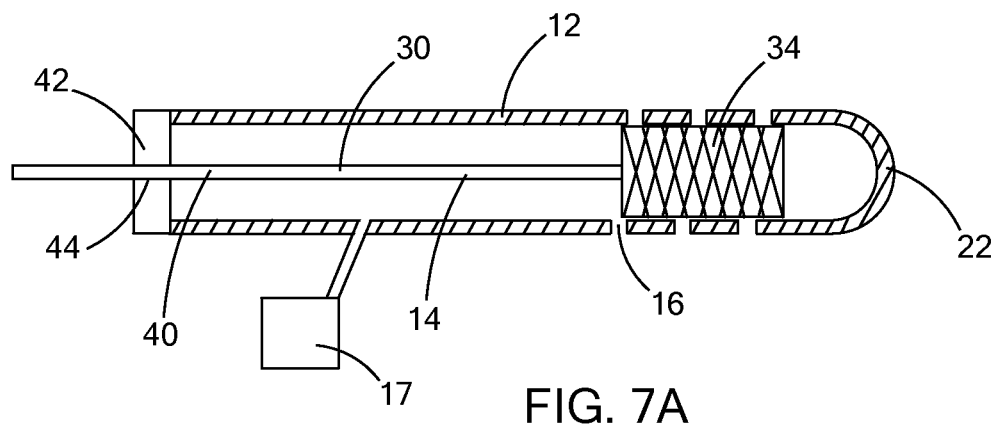
FIG. 7A is a schematic view of the tube of the cell collection system having a closed distal end and cap covering an open distal end of the tube.

With reference to FIG. 7A, as described previously, the tube 12 is configured for a vacuum to be applied to draw tissue into the perforations 16. The tube 12 is coupled to the vacuum source 17, which can be any suitable vacuum source capable of applying negative pressure to the tube 12. The closed distal end 22 of the distal portion 12b of the tube 12 assists in creating the vacuum within the tube 12. The tube 12 can include an open end 40 at the proximal portion 12a for allowing the brush 14 to be inserted into the tube 12. The system 10 can include a cap 42 for closing the open end 40 so that the vacuum can be more efficiently applied to the tube 12, functioning similar to the closed distal end 22. The cap 42 can include an opening 44 through which the shaft 30 of the brush 14 can extend. The cap 42 can be a one-piece structure coupled to the shaft 30 of the brush 14, or the cap 42 can be a two-piece structure for being installed after the brush 14 has been inserted into the tube 12. The cap 42 can be mounted to the tube 12 via a snap fit, threading, or other mechanical connection.

Figure 7B:
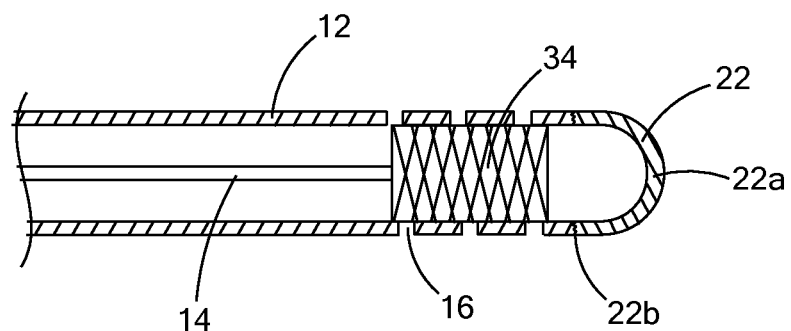
FIG. 7B is a schematic view of an alternative tube having a removable distal tip.
Figure 7C:
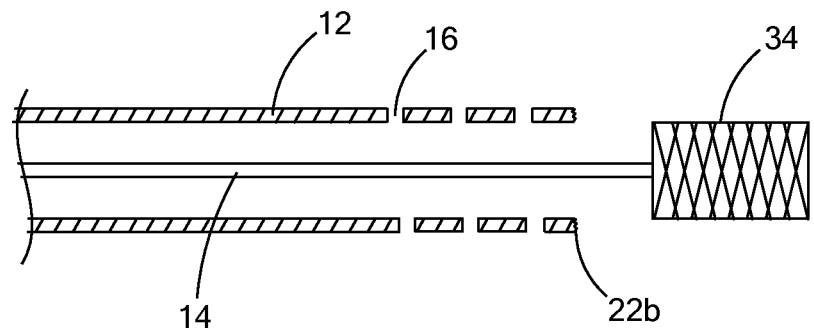
FIG. 7C is a schematic view of the tube of FIG. 7B having the removable distal tip removed and the brush extended out of the tube.

In another form, as shown in FIGS. 7B and 7C, the closed distal end 22 can be in the form of a removable tip 22a that is fitted to the distal end of the tube 12 via a mechanical connection 22b, such as a threaded connection, snap fit, or the like. The removable tip 22a can allow the brush 14 and the head portion 34 to be extended out of the distal end of the tube 12 after cell collection. This can allow the cells to be retrieved from the head portion 34 without having to pull the head portion 34 back through the length of the tube 12.

Figure 7D:
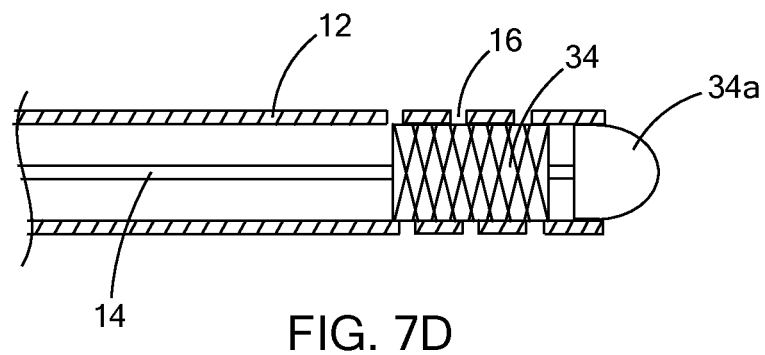
FIG. 7D is a schematic view of yet another tube having an open distal end and a brush having a sealing portion at its distal end to close the distal end of the tube.

In yet another form, as shown in FIG. 7D, the distal end of the tube 12 can be open, and the brush 14 can include a distal sealing portion 34a locating distally of the head portion 34. The sealing portion 34a can be made from a soft material such as silicone and be sized to correspond to the width of the lumen of the tube 12 such that the sealing portion 34a is sealingly engaged with the distal end of the tube 12, while still allowing the head portion 34 to be rotated or reciprocated within the tube 12 to collect cells. This sealing engagement can provide the same benefits as the closed distal end 22 to allow the vacuum to be created. When cell collection is complete, the brush 14 can be advanced distally to expose the head portion 34 to retrieve the cells therefrom. The sealing portion 34a can have an elongated dome shape to assist with the insertion of the tube 12 through the anatomy. The elongated shape of the sealing portion 34a also allows the brush to be reciprocated while maintaining the sealing connection with the tube 12.

In another form, the cap 42 can be integrally formed with the tube 12, and the opening 44 can be sized large enough to allow the head portion 34 to be inserted therein while retaining a close fit with the shaft 30. This is possible due to the bristles 32 being bendable and flexible. In this approach, the portion of the shaft 30 along the head portion 34 can be thinner to allow the bristles 32 additional space in which to bend.

Having described the general structure of the system 10, the use of the system 10 will now be described in further detail.

Figure 8:
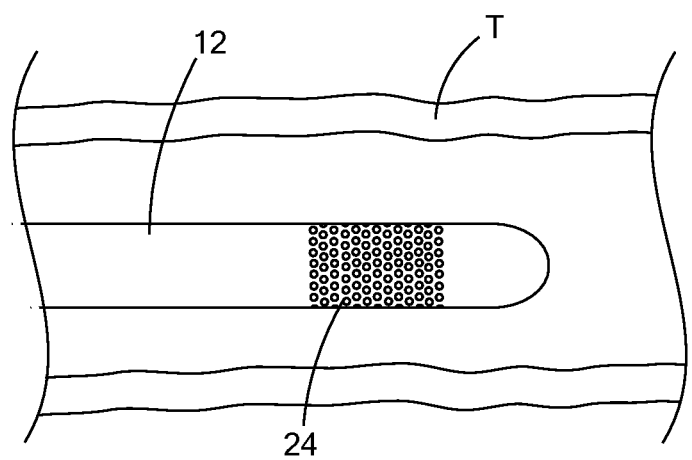
FIG. 8 is a schematic view of the tube inserted into a body cavity.
Figure 9:
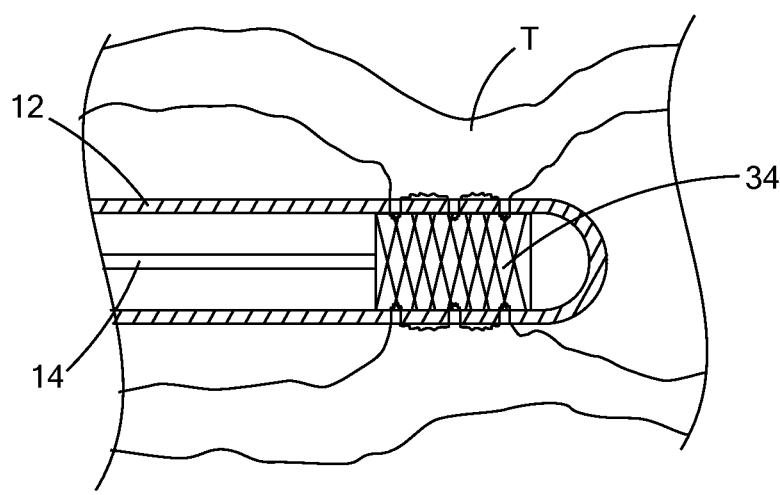
FIG. 9 is a schematic view of the tube with a vacuum applied to the tube to draw tissue of the body cavity into perforations of the tube.

With reference to FIGS. 8 and 9, the tube 12 can be inserted either directly into the patient's body via a body orifice, or can be inserted percutaneously using known methods. The tube 12 can be advanced through a body lumen of the patient toward the target site for cell collection. The flexible nature of the tube 12 can allow it to advance through various tortuous body lumen types. The position of the tube 12 can be monitored using known monitoring techniques, such as direct visualization or fluoroscopy.

Once the tube 12 has been inserted and positioned at the target site, the perforated portion 24 can be monitored and positioned in the desired area for cell collection. At this point, a vacuum can be applied to the tube 12 using the vacuum source 17. The vacuum will cause body tissue T adjacent the perforated portion 24 to be drawn into the perforations 16, providing an area of tissue for cell collection, as shown in FIG. 9.

Before, after, or during the application of the vacuum to the tube 12, the brush 14 can be inserted into the tube 12. Preferably, the brush 14 is inserted into the tube 12 prior to application of the vacuum, because inserting the brush 14 after the vacuum is applied could cause a temporary loss of the vacuum. The head portion 34 can be inserted toward the perforated portion so that the head portion 34 at least partially overlaps the perforated portion 24. The bristles 32 can contact the tissue that has been drawn into the perforations 16 to collect cells. The brush 14 can be rotated, reciprocated, or otherwise moved to increase the number of bristles 32 that contact the tissue. The bristles 32 can be generally restricted from contacting other areas of the target site because the vacuum applied causes the tissue to generally fill the perforations 16. The use of the tube 12 within the body cavity can improve the comfort of the patient because the bristles 32 of the brush 14 are limited from over-scraping or over-brushing the cavity.

By monitoring the placement of the tube 12, the tube 12 can provide accurate and consistent cell collection from the desired area. By inserting the brush 14 through the tube 12 toward the perforated portion 24, the brush 14 will generally not contact body tissue T outside of the target area. By drawing the tissue into the perforations 16, a consistent amount of tissue and contact between the tissue and the brush 14 can be achieved.

Once cell collection has been completed by the brush 14, the brush 14 can be retracted form the tube 12 where the cells can be retrieved from the brush 14 and analyzed using known methods. To collect an additional number of cells, another brush 14 can be inserted into the same tube 12. Thus, the use of the tube 12 can enable a large amount of cell collection by repeating the process with additional brushes 14.

At the conclusion of cell collection by the initial brush 14 and any additional brushes, the vacuum applied to the tube 12 can cease. The tube 12 can then be retracted from the patient. Alternatively, the tube 12 can be re-positioned to collect cells from another area, if desired. In the event this re-positioning is desired, the above described collection process can be repeated with the tube 12 in the different location.

The above described device and process therefore provides a robust and reliable method for collecting cells from a patient. The number and type of cells collected can be optimized, and an increased number of cells can be achieved with limited discomfort to the patient by limiting the interaction between the brush 14 and the body tissue to the tissue that is drawn into the perforations.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A system for collecting cells from bodily tissue, the system comprising:
   an elongate tube having a proximal portion and a distal portion and a lumen extending therebetween;
   an elongate cell collection device including a head portion sized and structured to engage the bodily tissue and remove cells therefrom, the cell collection device disposed within the lumen of the tube, the proximal portion of the tube configured such that the head portion of the cell collection device may be withdrawn proximally from the tube;
   a perforated portion of the tube including a plurality of perforations extending through a sidewall of the tube; and
   a vacuum source coupled to the tube for applying a vacuum to the lumen;
   wherein the head portion of the cell collection device and the perforated portion of the tube are sized and configured such that the head portion remains disposed within an outer diameter of the tube when the head portion at least partially longitudinally overlaps the perforated portion.

2. The system of claim 1, wherein the perforated portion is disposed around a complete circumference of the tube.

3. The system of claim 1, wherein the perforated portion is disposed around a portion of the circumference of the tube that is less than the complete circumference of the tube.

4. The system of claim 2, wherein the perforated portion is disposed at the distal portion of the tube.

5. The system of claim 1, wherein the distal portion of the elongate tube is flexible.

6. The system of claim 1, wherein the tube is formed by a sidewall having a thickness of 0.2 mm to 0.8 mm.

7. The system of claim 1, wherein individual ones of the plurality of perforations have a diameter of 1-3 mm.

8. The system of claim 1, wherein the distal portion includes a closed end.

9. The system of claim 1, wherein the distal portion of the tube includes a temporarily removable tip.

10. The system of claim 1, wherein the cell collection device includes a sealing portion disposed at a distal end thereof that sealingly engages a sidewall of the tube, the tube includes an open distal end, and the sealing portion is moveable distally out of the open distal end of the tube to expose the head portion.

11. The system of claim 1, wherein the head portion comprises a plurality of bristles.

12. The system of claim 1, wherein the lumen has a diameter, and the head portion has a diameter that is greater than the diameter of the lumen.

13. The system of claim 1, wherein the lumen has a diameter, and the head portion has a diameter that is less than or equal to the diameter of the lumen.

14. The system of claim 1, wherein the perforated portion is 1-2 cm long.

15. The system of claim 1, wherein the wherein the head portion of the cell collection device and the perforated portion of the tube are sized and configured such that an outermost surface of the head portion remains disposed within an outer diameter of the tube when the head portion overlaps the perforated portion.

16. A medical device for collecting cells, the device comprising:
   an elongate tube having a tubular sidewall, a proximal portion, and a distal portion, wherein the sidewall defines a lumen extending along the length of the tube;
   a plurality of perforations disposed in the distal portion and extending through the sidewall;
   a closed distal tip of the tube disposed distally of the plurality of perforations;
   an elongate brush disposed within the lumen of the tube, the brush having a shaft with a head portion coupled to a distal end of the shaft for collecting cells disposed within the plurality of perforations; and
   wherein the perforations extend through the sidewall and the lumen is in fluid communication with an exterior of the tube; and
   wherein negative pressure applied within the lumen causes body tissue disposed adjacent the exterior of the tube to be presented to the interior of the tube through the perforations;
   wherein the head portion and the perforated portion of the tube are sized and configured such that an outermost surface of the head portion remains disposed within an outer diameter of the tube when the head portion at least partially longitudinally overlaps the perforated portion.

17. The device of claim 16, wherein individual ones of the plurality of perforations have a circular shape and a diameter of 1-3 mm.

18. The device of claim 17, wherein individual ones of the plurality of perforations have a slotted shape having a length of 3-10 mm and a width of 1-3 mm.

19. The device of claim 16, wherein the tube is flexible and made from polyether block amide.

20. The device of claim 16, wherein the head portion comprises a plurality of bristles, and an outer circumference of the head portion contacts an inner circumference of the tube.

21. A method for collecting cells, the method comprising:
   inserting an elongate tube into a body cavity, wherein the tube includes a sidewall defining a lumen extending therealong, and wherein the tube includes a perforated portion including a plurality of perforations extending through the sidewall of the tube;
   longitudinally aligning a head portion of a brush at least partially with the perforated portion of the tube, wherein the head portion overlaps the perforated portion, wherein the head portion and the perforated portion of the tube are sized and configured such that an outer surface of the head portion remains disposed within an outer diameter of the tube when the head portion overlaps the perforated portion;
   applying a vacuum to the lumen of the tube;
   in response to applying the vacuum, drawing body tissue into the plurality of perforations; and
   in response to drawing the body tissue, contacting the tissue with the brush to collect cells from the tissue.

22. The method of claim 21, wherein the step of aligning the head portion occurs prior to applying the vacuum.

23. The method of claim 21, wherein the step of aligning the head portion occurs after applying the vacuum.

24. The method of claim 21 further comprising rotating the head portion.

25. The method of claim 21 further comprising retracting the brush from the lumen and inserting a second brush into the lumen and collecting additional cells.

26. The method of claim 21 further comprising reciprocating the head portion longitudinally relative to the perforated portion.

27. The method of claim 21, wherein the head portion comprises a plurality of bristles, and the bristles are compressed radially inward with the head portion disposed within the tube.

28. The method of claim 27, wherein the bristles expand outward with the head portion retracted out of the tube.

* * * * *